United States Patent [19]
Chartrain et al.

[11] Patent Number: 5,900,368
[45] Date of Patent: May 4, 1999

[54] PROCESS FOR BIOREDUCTION OF BISARYL KETONE TO BISARYL ALCOHOL

[75] Inventors: Michel M. Chartrain, Westfield, N.J.; Hywyn R.O. Churchill, Radford, Va.; Woo-Baeg Choi, North Brunswick; Shigeko Yamazaki, Edison, both of N.J.

[73] Assignee: Merck & Co., Inc., Rahway, N.J.

[21] Appl. No.: 08/924,938

[22] Filed: Sep. 8, 1997

Related U.S. Application Data

[60] Provisional application No. 60/026,249, Sep. 17, 1996.

[51] Int. Cl.$^6$ .............................. C12P 13/00; C12P 13/02; C12P 7/22
[52] U.S. Cl. ........................... 435/128; 435/129; 435/156; 435/280; 435/911; 435/913; 435/930
[58] Field of Search ..................................... 435/156, 128, 435/129, 911, 930, 913, 280

[56] References Cited

U.S. PATENT DOCUMENTS

| | | |
|---|---|---|
| 4,464,235 | 8/1984 | Simon et al. . |
| 4,879,233 | 11/1989 | Charney ................................. 435/129 |
| 4,948,732 | 8/1990 | Charney . |
| 4,981,796 | 1/1991 | Ogura et al. . |
| 5,391,495 | 2/1995 | Patel et al. ............................... 435/911 |
| 5,393,663 | 2/1995 | Patel et al. ............................... 435/280 |
| 5,427,933 | 6/1995 | Chen et al. .............................. 435/156 |
| 5,474,919 | 12/1995 | Chartrain et al. ....................... 435/911 |
| 5,608,070 | 3/1997 | Alexander et al. . |
| 5,622,977 | 4/1997 | Warrellow et al. . |

*Primary Examiner*—Herbert J. Lilling
*Attorney, Agent, or Firm*—Richard C. Billups; David L. Rose; Curtis C. Panzer

[57] ABSTRACT

The present invention is directed to an improved process for making PDE IV inhibitors. In specific, this application describes a process for making and purifying a chiral bisaryl alcohol, an intermediate compound necessary for the preparation of PDE IV inhibitors such as CDP 840, by asymmetric bioreduction of a pro-chiral ketone. Furthermore, the bioprocess provides for production of each enantiomer of a bisaryl alcohol at elevated optical purity.

This invention takes advantage of a microorganism's ability to reduce a pro-chiral bisaryl ketone to the chiral bisaryl alcohol. The alcohol is readily isolated from the media by solvent extraction, crystallography, or other purification method known to the skilled artisan. The chiral alcohol can then be converted to a PDE IV inhibitor, such as CDP 840, by methods well known in the art.

5 Claims, No Drawings

PROCESS FOR BIOREDUCTION OF BISARYL KETONE TO BISARYL ALCOHOL

This application claims the benefit of U.S. provisional application No. 60/026,249 filed Sep. 17, 1996.

BACKGROUND OF THE INVENTION

This invention relates to a process for making phosphodiesterase IV (PDE IV) inhibitors which are useful in treating asthma and other diseases mediated by PDE IV. More particularly, this application describes a process for making and purifying a chiral bisaryl alcohol, an intermediate compound necessary for the preparation of PDE IV inhibitors such as CDP 840, by asymmetric bioreduction of a pro-chiral ketone.

Many hormones and neurotransmitters modulate tissue function by elevating intra-cellular levels of adenosine 3', 5'-cyclic monophosphate (cyclic AMP or cAMP). The role of cAMP as a second messenger is well recognized. It is responsible for transducing the effects of a variety of extra-cellular signals, including hormones and neurotransmitters. The level of intracellular cAMP is regulated through both its synthesis by adenyl cyclases and degradation by cyclic nucleotide phosphodiesterases (PDE). PDEs form a family of at least seven enzyme isotypes (I–VII) which differ in their affinity for cAMP and/or cGMP, subcellular localization and regulation (Beavo J. A. and Reifsnyder D. H. (1990) Trends Pharmacol. Sci. 11 150–155; Conti M. et al., (1991) Endocrine Rev. 12 218–234). The clinical effects of a number of drugs can be rationalized on the basis of their selectivity for a particular PDE isotype. For example, the cardiotonic drugs milrinone and zaprinast are PDE III and PDE V inhibitors respectively. (Harrison S. A. et al., (1986) Mol. Pharmacol. 29 506–514; Gillespie P. G. and Beavo J. (1989) Mol. Pharmacol. 36 773–781). The anti-depressant drug, rolipram functions as a selective PDE IV inhibitor. (Schneider H. H. et al., (1986) Eur. J. Pharmacol. 127 105–115.).

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) J. Immunol. 148 2503–2510) and eosinophils (Dent G. et al., (1991) Br. J. Pharmacol. 103 1339–1346) and that inhibition of this isotype is associated with the inhibition of cell activation. Consequently PDE IV inhibitors are currently being developed as potential anti-inflammatory drugs particularly for the prophylaxis and treatment of asthma.

Several compounds that act as PDE IV inhibitors, including CDP 840, as well as methodology for their production, are disclosed in WO 94/14742, published Jul. 7, 1994, which is hereby incorporated by reference. These compounds are useful as anti-inflammatory drugs, particularly for prophylaxis and treatment of asthma as well as for treatment of other inflammatory diseases. However, WO 94/14742 does not describe an efficient chemical means for making a chiral bisaryl alcohol intermediate for use in production of PDE IV inhibitors. The benefit of such invention is a more efficient means of making PDE IV inhibitor compounds that require a bisaryl alcohol intermediate, such as CDP 840, and greater yield.

The present invention describes a biotransformation process for the production of a specific chiral alcohol intermediate important in the chemical synthesis of PDE IV inhibitors. There is currently no known chemical method for production of a chiral bisaryl alcohol of the invention, which is a key intermediate used to make CDP 840 and other PDE IV inhibitors. The chiral compound of the invention is a necessary intermediate in producing PDE IV inhibitors. Its exceptional optical purity, when made by the bioprocess of the invention, allows production of the PDE IV inhibitor in fewer steps and greater yield than if a synthetically produced racemic mixture were used.

Microorganisms capable of reducing a prochiral bisaryl ketone to a chiral bisaryl alcohol for synthesizing PDE IV inhibitors, such as CDP 840, are used in the invention. Moreover, the enantiomeric purity of the compound of the invention produced in microorganisms permits a greater yield of PDE IV inhibitor and requires less steps than chemical synthesis of the intermediates for making the inhibitors. Thus, the present invention provides an optically pure intermediate for use in making PDE IV inhibitors and permits synthesis of the inhibitor in fewer steps.

SUMMARY OF THE INVENTION

The present invention is directed to an improved process for making PDE IV inhibitors. In specific, this application describes a process for making and purifying a chiral bisaryl alcohol, an intermediate compound necessary for the preparation of PDE IV inhibitors such as CDP 840, by asymmetric bioreduction of a pro-chiral ketone. Furthermore, the bioprocess provides for production of each enantiomer of a bisaryl alcohol at elevated optical purity.

The present invention takes advantage of a microorganism's ability to reduce a prochiral bisaryl ketone to a chiral bisaryl alcohol. The alcohol can be isolated from the media by chromatography or other purification method known to the skilled artisan. The chiral alcohol can then be converted to a PDE IV inhibitor, such as CDP 840, according to methods described in WO 94/14742.

DETAILED DESCRIPTION OF THE INVENTION

Certain microorganisms, including yeasts and fungi, are employed for the bioconversion of a prochiral bisaryl ketone of formula II,

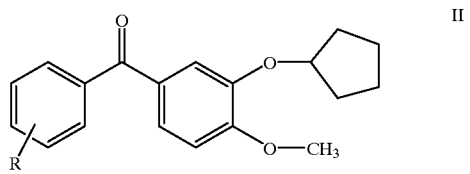

wherein R is optionally positioned ortho or para on the phenyl ring and is selected from the group consisting of:

(i) hydrogen
(ii) —NH$_2$,
(iii) —NH—C(O)—NH—CH$_3$, and
(iv) —SO2—NH$_2$ .

Through a reduction mechanism, the microorganism converts the bisaryl ketone to its corresponding chiral bisaryl alcohol of formula I,

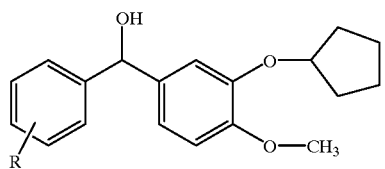

wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$.

The resulting bisaryl alcohol has high optical purity (ee) of greater than 90%. In a preferred embodiment the bisaryl alcohol product has an ee of greater than 92%. In the most preferred embodiment ee is greater than 96%. Thus, the invention provides a novel alternative to chemical synthesis of a bisaryl alcohol compound, comprising the bioconversion of a bisaryl ketone to a single enantiomeric form having great optical purity.

In one embodiment the invention is directed to a process of preparing a chiral bisaryl alcohol compound of formula I,

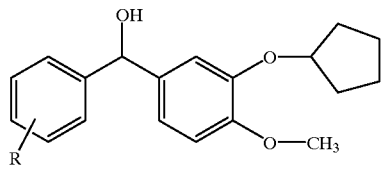

wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$.

The process comprises the following three steps.

The first step comprises:
(a) Cultivating a microorganism selected from yeast and fungi in a culture media suitable for the growth of the microorganism, which microorganism is capable of bioconverting a bisaryl ketone to a bisaryl alcohol by reduction.

The fermentation process of the present invention utilizes a readily prepared-culture medium suitable for growth of a microorganism selected by the practitioner. Culture medium is a mixture which provides essential nutrients for growth of the yeast or fungal cells of the invention. The components necessary for a suitable culture media are readily obtainable from a commercial source and prepared by known methods in the art. A suitable culture media for growing fungi can comprise 4 g/L yeast extract, 20 g/L malt extract and 4 g/L glucose. To culture yeast, Saboureau dextrose (Difco, Detroit, Mich.) is commercially available and comprises 10 g/L Neopeptone and 20 g/L dextrose. The invention contemplates the precise amounts and types of ingredients necessary to sustain the particular microorganism chosen can be optimized or modified to meet the needs of the skilled artisan. A suitable range for pH of the culture medium is from about 5.5 to 7.0. The microorganisms can be cultivated at a temperature from about 25° C.–30° C. However, wider ranges for pH and temperature are not outside the scope of the invention.

The present invention utilizes microorganisms suitable for bioreduction of a bisaryl ketone to bisaryl alcohol selected from certain yeasts and fungi. They include, but are not limited to, fungal strains *Aspergillus nidulans* MF 121, *Rhodotoruolla pilimanae* ATCC 32762 which produce the "B" enantiomer of the bisaryl alcohol. The "A" enantiomer can be produced by the yeast strain *Hansenula holstii* (MY 1538).

The second step comprises:
(b) Adding to the culture media an amount of a bisaryl ketone having structural formula II,

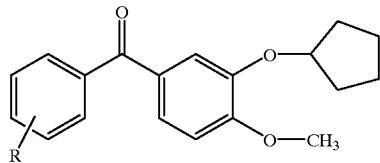

wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$.

The bisaryl ketone substrate is added to culture media containing the microorganism and is reduced to the chiral bisaryl alcohol of the invention. The process of bioconversion of the bisaryl ketone to the bisaryl alcohol product of the invention is shown in Scheme I:

SCHEME I

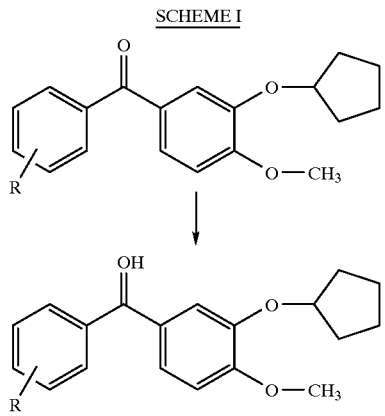

The final step comprises:
(c) Recovering the bisaryl alcohol product from the culture media.

The chiral bisaryl alcohol product can be readily isolated from the culture media and purified using one of many chemical purification techniques known to the skilled artisan, such as, but not limited to, high performance liquid chromatography, solvent extraction, or crystallization.

After the bisaryl alcohol is purified it can be used as an intermediate for synthesis of CDP 840 or other PDE IV inhibitor. Methods for such synthesis are found in WO 94/14742 published Jul. 7, 1994. In one instance, described in Scheme II below, the alcohol is activated toward nucleophilic displacement by conversion to a suitable leaving group X by methods known in the art, wherein R is optionally positioned ortho or para on the phenyl ring and is selected from the group consisting of hydrogen, —NH$_2$, —NH—C(O)—NH—CH$_3$, and —SO$_2$—NH$_2$ and X is a halogen selected from chlorine, fluorine, bromine and iodine, OSO$_2$R', or OPO(OR')$_2$ where R' is alkyl, aryl, or substituted aryl. (See March J. (1992) *Advanced Organic*

*Chemistry Reactions, Mechanisms, and Stucture* 4th ed. John Wiley and Sons New York. p. 352.; Thompson et al. (1993) *J. Org. Chem.* 22, 5886–88.). The activated intermediate then undergoes substitution with inversion of stereochemistry by reaction with a metallated picoline† nucleophile (M=Li, Na, K, Mg, Ce, or Cu) (†Osuch et al. (1956) *J. Am. Chem. Soc.* 78, 1723).

The following is a schematic representation of the synthesis of the PDE IV inhibitor CDP-840 from the chiral bisaryl alcohol of the invention:

SCHEME II

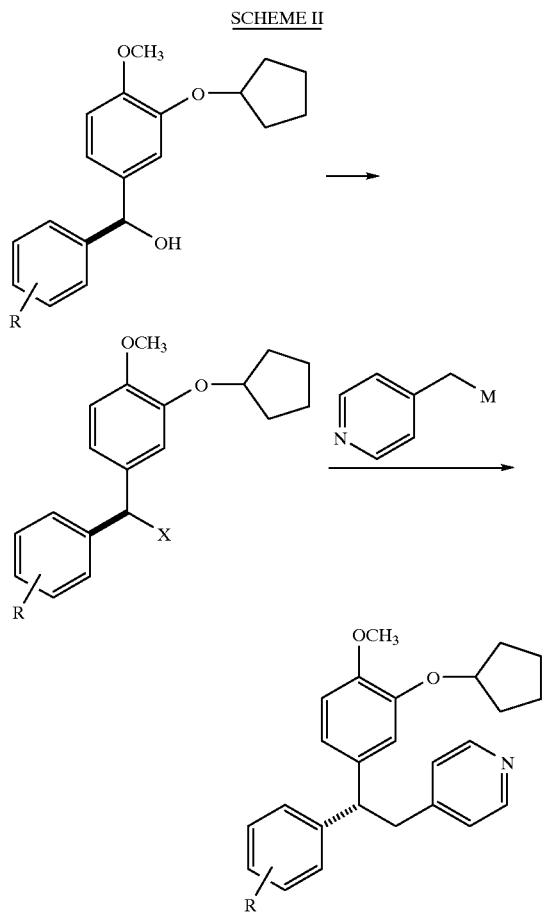

When used herein "optically pure" or "ee" shall be defined as percent of one enantiomer-percent of other enantiomer, where the total percent of the two enantiomers together equals 100%.

EXAMPLE 1

Chemicals. All chemicals are of reagent grade and purchased from either Fisher Scientific (Springfield, N.J.) or Sigma Chemical Co. (St. Louis, Mo.). Hysoy peptone may be obtained from Sheffield (Norwich, N.Y.); yeast extract and Sabouraud dextrose and nutrient broth may be purchased from Difco (Detroit, Mich.).

Racemic diaryl alcohol is prepared as follows. Isovanillin (100 g, 0.65 mol) and potassium carbonate (138.2 g, 1.12 mol) are added to dimethylsulfoxide (DMSO) (600 ml) portion-wise at room temperature. The mixture is heated to 60° C. and cyclopentyl bromide (112 mL, 1.12 mol) is added over a 30 min period at 60° C. The mixture is aged at 60° C. for 14 h, and then cooled to room temperature. Water (600 mL) is added in one portion and the solution is stirred for 30 min. The mixture is extracted twice with toluene (800 mL, 400 mL). The combined organic layers are washed with a dilute HCl aqueous solution (0.2 N, 0.8 L) and with water (0.6L×2). The organic layer is concentrated to 1 L. To the above toluene solution, phenylmagnesium bromide solution in ether (230 mL, 3M) is added at −10° C. and the mixture is aged for 30 min below 0° C. 1 N aqueous HCl solution (700 mL) and ethyl acetate (700 mL) are added successively and the layers are separated. The organic layer is washed with water (500 mL×2) and concentrated to dryness. Under the foregoing conditions, crystallization of the crude alcohol in 1:6 ethyl acetate/hexanes mixture (1.4 L) resulted in 167.8 g of a white solid (87% yield).

To make the chiral bisaryl alcohol of the invention, the bisaryl ketone is prepared from racemic bisaryl alcohol as follows.

The alcohol (167 g, 0.56 mol) is dissolved in 10:1 tetrahydrofuran:water (660 mL) and RuCl$_3$ (2.1 g, 1.8 mol %) is added at room temperature. The mixture is then warmed to 50° C. and t-butyl hydrogen peroxide (300 mL, 70% in water) is added drop-wise. At this point the mixture should be at reflux. Upon completion, the mixture is cooled to room temperature and washed with Na$_2$SO$_3$ (1.2 L, 2 N) followed by water (600 mL×2). The organic layer is concentrated to dryness and the resulting solid is recrystallized from 3:1 hexanes:ethyl acetate (2 L) at 0° C. to give 142.2 g of a white solid (72% yield).

EXAMPLE 2

The present invention defines a bioprocess that reduces bisaryl ketone to its corresponding bisaryl alcohol using a microorganism selected from yeasts or fungi. The present example demonstrates the use of yeast *Rhodotorulla pilimanae* strain (ATCC 32762) in the bioreduction process of the invention. This strain is described as an example of one microorganism that may be employed in the present invention, while others include *Aspergillus nidulans* MF 121, and *Hansenula holstii* (MY 1538), and is not meant to place a limitation on the scope of the invention.

Materials and Methods

The following methods indicate the amounts of reagents used by the Applicant and the resulting yield is indicated.

Screening Methods.

Microorganisms (Merck Microbial Resources Culture Collection, Merck & Co., Rahway N.J.) may be preserved on Sabouraud dextrose agar slants comprising 18 g/L agar, 10 g/L Neopeptone and 20 g/L dextrose, or YME agar slants comprising 4 g/L yeast extract, 20 g/L malt extract, 4 g/L glucose and 18 g/L agar at 4° C. for yeasts and fungi respectively. Erlenmeyer flasks (250-mL) containing 25 mL of the appropriate medium are inoculated with the desired microorganism and incubated on an orbital shaker (220 r.p.m.) at 28° C. After 48 hours of cultivation, 25 mg of bisaryl ketone dissolved in 1 mL of ethanol is added to each flask (1 g/l final concentration) to initiate the bioconversion. The flasks are returned to the same incubation conditions as described above. The presence of the desired corresponding reduced compound can be detected after 48 hours by HPLC analysis of the supernatant diluted (1:5) with acetonitrile.

Analytical methods.

Reverse phase assay: A Rainin HPLC system (Rainin, Woburn, Mass.) equipped with a Zorbax RX-C8 column (4.6 mm×25 cm) (Mac-Mod Analytical, Chadds Ford, Pa.), may be employed for the separation of the bisaryl ketone and its corresponding alcohol. Separation is achieved by isocratic elution, employing a mobile phase comprised of acetonitrile and acidified water (0.1% phosphoric acid) [50:50; v/v] at a flow rate of 1.0 mL/min. Detection is performed at 210 nm and at 22° C., with the ketone eluting after the alcohol (12.4 and 9.3 min respectively under Applicant's conditions). The chiral assay may be performed on a similar HPLC system, such as a Chiracel OJ (4.6 mm×25 cm) column and using a mobile phase made up of ethanol:hexane (15:85; v/v) to be delivered at a flow rate of 0.6 mL/min. Detection is performed at 210 nm. Under Applicant's conditions alcohol A and alcohol B eluted after 10.2 min and 11.8 min respectively.

Results

Screening results.

A total of 310 microorganisms (53 bacteria, 113 yeasts and 144 fungi) were evaluated for their ability to bioreduce the bisaryl ketone to its corresponding alcohol. HPLC analyses of extracts indicated that 8 strains of microorganisms were capable of producing a single enantiomer with good optical purity (See Table 1). The yeast strain *Rhodotorulla pilimanae* (ATCC 32762) which produced the "B" enantiomer with an ee>96% was further selected for the production of preparative amounts of chiral bisaryl alcohol.

Production at the preparative scale.

The scale-up of the asymmetric bioreduction process may be performed in 23 L fermentors (Chemap Inc., South Plainfield, N.J.). A volume of 16 L of production medium (Sabourau dextrose) and 16 mL of P2000 antifoam (Poly Glycol, Dow Chemical Co., Midland, Mich.) are sterilized in situ at 121° C. for 25 min. Five hundred mL of a 24-hour old second stage seed is used to inoculate the bioreactor, which is operated at 28° C. with an agitation set at a minimum of 220 r.p.m., an aeration of 6 L of air per minute, and a back pressure of 0.6 bar. Dissolved oxygen tension is maintained at 30% of initial saturation by computer controlled ramping of the agitation and by manually increasing the air flow. The bioreduction is then initiated 50 hrs after inoculation by addition of 16 g of bisaryl ketone (final concentration 1 gl ) dissolved in 640 mL of ethanol.

FIG. 1 shows that a maximum bisaryl alcohol concentration of about 100 mg/l may be achieved 48 hrs after the addition of the bisaryl ketone. No further increases in this titer were observed by Applicant after that time, and a yield of about 10% was therefore achieved in this preparative scale experiment.

The whole broth (16 L) containing about 1.65 g of alcohol was extracted with one volume (16 L) of ethylacetate. The organic layer was vacuum concentrated 27-fold yielding 600 mL of liquors containing 1.44 g of alcohol. The liquor was subsequently chromatographed onto a silica gel column using 15:85 ethyl acetate:hexanes mixture. Fractions containing the alcohol are combined and concentrated to dryness. The resulting solid is finally crystallized from hexanes to give 0.92 g of a white solid.

The authenticity of the desired product was confirmed by proton NMR. The assignments for the bisaryl alcohol are: ppm in CDCl3, 7.4–7.2 (m, 5H's, aromatic), 6.9–6.7 (m, 3H's, aromatic), 5.8 (d, 1H, benzylic), 4.7 (m, 1H, O—CH), 3.8 (s, 3H's, CH$_3$), 2.2 (d, 1H, OH), 1.9–1.5 (m, 8H's, 2(CH2—CH2)). The enantiomeric excess of the purified bisaryl alcohol was evaluated to be greater that 96% by normal phase chiral HPLC.

In conclusion, the invention by way of the present example describes a facile and scaleable method for the preparation of optically pure bisaryl alcohol (ee>96% when employing yeast strain *Rhodotorulla pilimanae*, ATCC 32762) of the "B" form by asymmetric bioreduction of the ketone precursor. Production of the "A" enantiomer, using MY 1538 can also be scaled up for the production of preparative amounts of that enantiomer.

What is claimed is:

1. A process for preparing a chiral bisaryl alcohol compound of formula I,

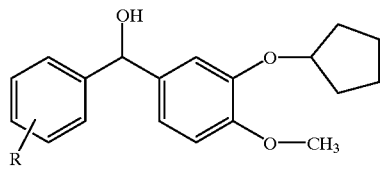

wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$,
comprising the steps of:
(a) cultivating fungi in a culture media capable of sustaining the microorganism, which microorganism is capable of bioconversion of bisaryl ketone to bisaryl alcohol by reduction;
(b) adding to the culture media an amount of a bisaryl ketone having structural formula II,

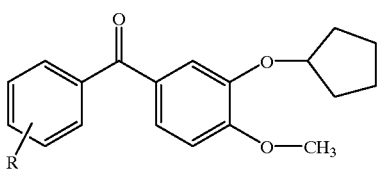

wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$; and
(c) recovery of the bisaryl alcohol from the culture media.

2. A process for preparing a chiral bisaryl alcohol compound of formula I,

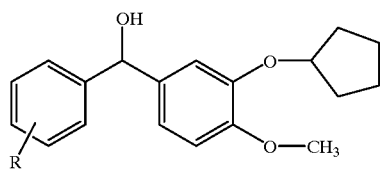

wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$,
comprising the steps of:
(a) cultivating *Rhodoturulla pilimanae* (ATCC 32762) in a culture media capable of sustaining the microorganism, which microorganism is capable of bioconversion of bisaryl ketone to bisaryl alcohol by reduction;

(b) adding to the culture media an amount of a bisaryl ketone having structural formula II,

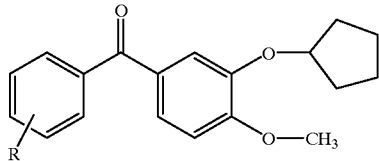

II wherein R is optionally positioned ortho or para on the phenyl ring and is selected from the group consisting of:
(i) hydrogen,
(ii) —NH$_2$,
(iii) —NH—C(O)—NH—CH$_3$, and
(iv) —SO$_2$—NH$_2$; and (c) recovering bisaryl alcohol from the culture media by isolation and purification wherein the optical purity of the bisaryl alcohol is greater than 90% ee.

3. The process according to claim 2 wherein the recovered bisaryl alcohol has an optical purity in the range greater than 92% ee.

4. The process according to claim 2 wherein the optical purity is greater than 96% ee.

5. The process according to claim 2 whereby the bisaryl alcohol product is recovered by a method selected from reverse phase high performance liquid chromatography, solvent extraction or crystalization.

* * * * *